United States Patent
Winters et al.

(10) Patent No.: US 11,479,432 B1
(45) Date of Patent: Oct. 25, 2022

(54) BARRIER ENVELOPE DISPENSER

(71) Applicant: FLOW DENTAL PRODUCTS, LLC, Deer Park, NY (US)

(72) Inventors: William Winters, White Plains, NY (US); Terrence McLaughlin, Kings Park, NY (US)

(73) Assignee: FLOW DENTAL PRODUCTS, LLC, Deer Park, NY (US)

( * ) Notice: Subject to any disclaimer, the term of this patent is extended or adjusted under 35 U.S.C. 154(b) by 60 days.

(21) Appl. No.: 17/249,270

(22) Filed: Feb. 25, 2021

Related U.S. Application Data

(60) Provisional application No. 63/036,229, filed on Jun. 8, 2020.

(51) Int. Cl.
*B65H 29/00* (2006.01)
*A61B 6/14* (2006.01)
*A61B 6/00* (2006.01)

(52) U.S. Cl.
CPC ............ *B65H 29/00* (2013.01); *A61B 6/14* (2013.01); *A61B 6/4216* (2013.01)

(58) Field of Classification Search
CPC . A47F 1/126; B65D 83/0038; B65D 83/0817; B65D 83/0858; B65H 29/00
USPC ....... 221/226, 227, 228, 229, 230, 231, 268, 221/271
See application file for complete search history.

(56) References Cited

U.S. PATENT DOCUMENTS

| | | | | |
|---|---|---|---|---|
| 4,465,208 A * | 8/1984 | Buban | ................ | B65D 83/0823 206/800 |
| 4,724,974 A * | 2/1988 | Marqua | ............... | B65D 83/0038 217/65 |
| 5,337,897 A * | 8/1994 | Yablans | ............. | B65D 83/0858 206/823 |
| 6,053,356 A * | 4/2000 | Emoff | ................ | B65D 83/0817 221/45 |
| 8,490,828 B2 * | 7/2013 | Kaiser | ................ | B65D 83/0823 206/358 |
| 9,738,433 B2 * | 8/2017 | Hogg | ..................... | B65D 83/02 |

FOREIGN PATENT DOCUMENTS

| | | | | |
|---|---|---|---|---|
| DE | 202004010639 U1 * | 10/2004 | ......... | B65D 83/0864 |
| DE | 202010009056 U1 * | 10/2010 | ............... | A47F 1/06 |
| FR | 3113491 A1 * | 2/2022 | | |

* cited by examiner

*Primary Examiner* — Patrick H Mackey
(74) *Attorney, Agent, or Firm* — Gottlieb, Rackman & Reisman, P.C.

(57) ABSTRACT

A dispenser of barrier envelopes is formed of a pair of selectively interlocking open-top box-like structures. When interlocked, the pair of structures forms an interior chamber that is configured to store and protect one or more barrier envelopes inside from external contaminants such as viruses, bacteria and/or fungi. The dispenser of barrier envelopes includes a through opening for the purpose of dispensing the one or more envelopes to a user, and a spring in its interior chamber for directing the one or more envelopes toward the through opening.

20 Claims, 6 Drawing Sheets

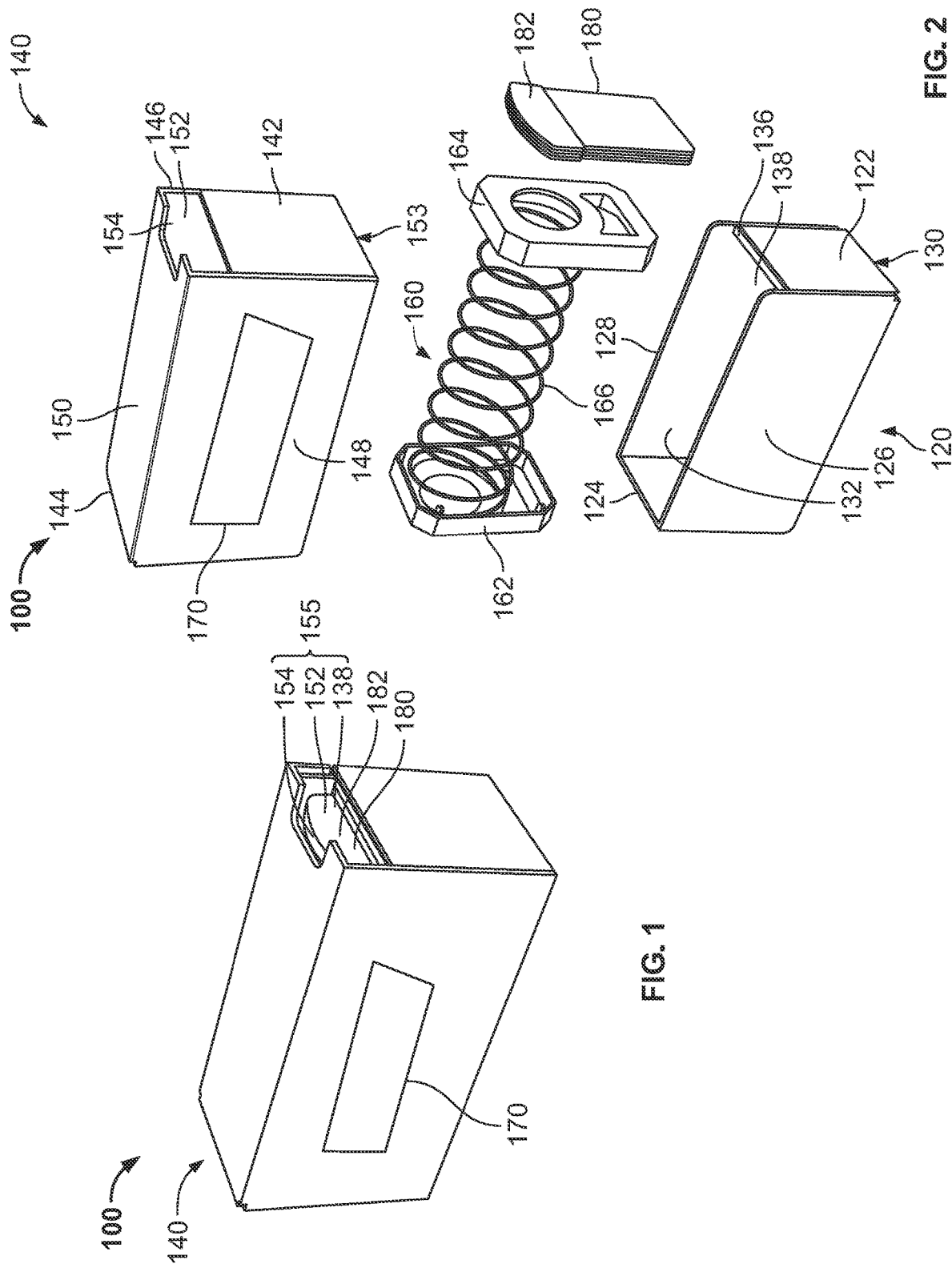

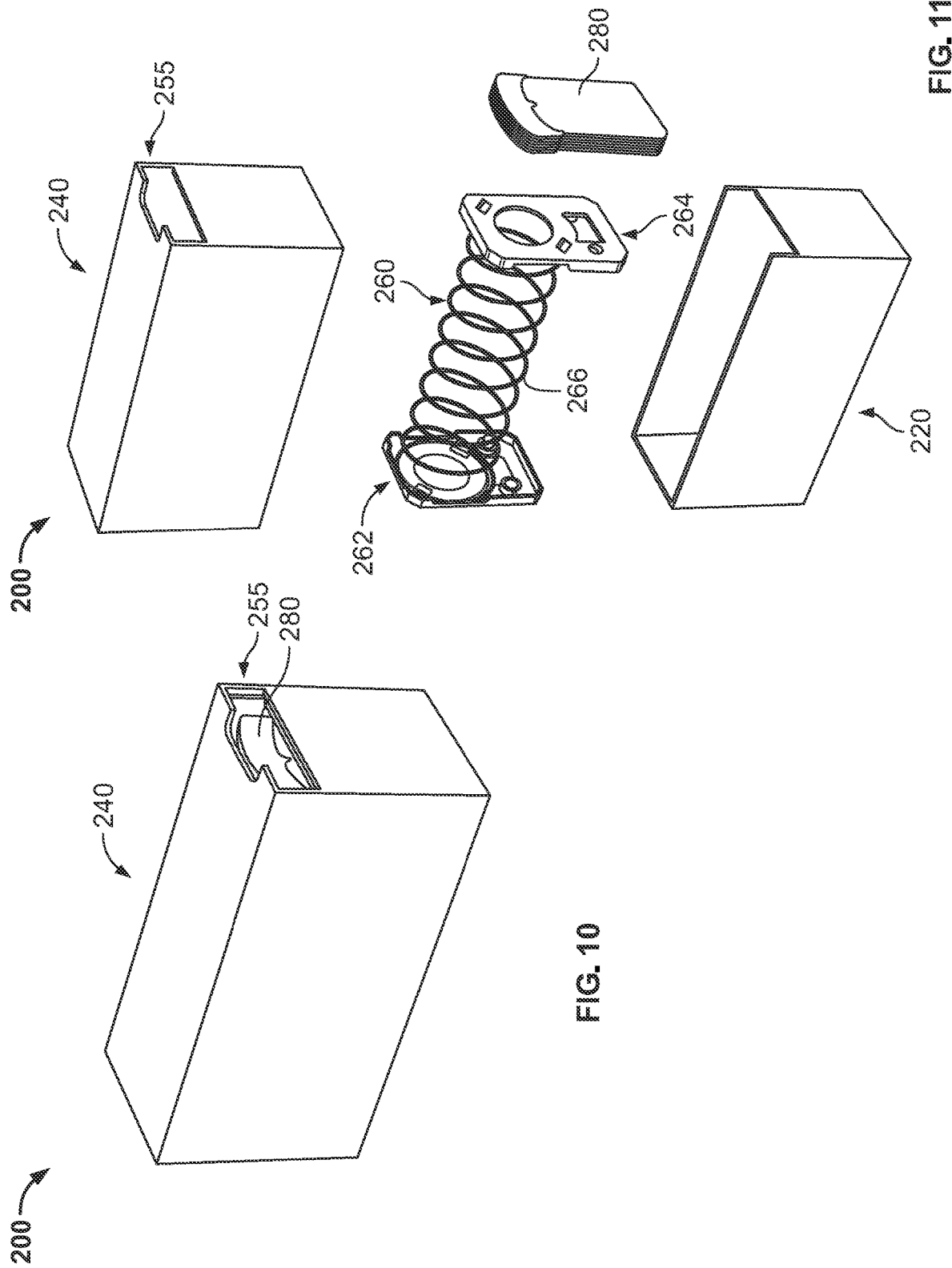

BARRIER ENVELOPE DISPENSER

CROSS-REFERENCE TO RELATED APPLICATION

This application claims priority under 35 U.S.C. § 119 to U.S. Provisional Patent Application No. 63/036,229, filed on Jun. 8, 2020, the disclosure of which is incorporated by reference herein in its entirety.

TECHNICAL FIELD

The present invention relates to a barrier envelope dispenser, and more particularly, to a dispenser of barrier envelopes having a spring-loaded member that facilitates the ejection of the envelopes from the dispenser and a method for utilizing the same.

DISCUSSION OF THE RELATED ART

A photostimulable phosphor (PSP) plate is an X-ray detector that is commonly used in the field of dentistry for obtaining a two-dimensional digital X-ray image of a part of a patient's mouth. The PSP plate is inserted in a patient's mouth behind a tooth or other body part to be examined, and an X-ray exposure is then made. The exposed PSP plate is subsequently inserted into a PSP reader which reads the PSP plate and generates a digital X-ray image of the body part of interest. The PSP reader can also be used to erase the exposed PSP plate after the reading operation. Subsequently, the erased PSP plate can be reused to obtain another X-ray image.

The process of exposing, reading and erasing a PSP plate can be repeated numerous times during a workday in a dental office. Therefore, a single PSP plate can be used over and over again on a plurality of different patients in order to capture a relatively large number of X-ray images.

In order to reduce the likelihood of intraoral transmission of contaminants between different patients or from a dental practitioner to a patient via a PSP plate, each PSP plate is inserted into a single-use barrier envelope which is then sealed prior to insertion in a patient's mouth. After an X-ray exposure, the PSP plate is removed from the envelope—the envelope is then discarded—and the plate is inserted into a reader for reading and subsequently erasing the X-ray image. The erased PSP plate can then be inserted in another barrier envelope for future use.

In dental offices, the barrier envelopes are generally stored in a drawer or in an open container. A dental practitioner can come into contact with a plurality of envelopes at once when accessing the interior of the drawer or container for withdrawing one envelope from the group. This practice is unsanitary because when the medical practitioner's hands are contaminated, the contamination could spread to a large number of envelopes, and subsequently, to a large number of patients.

Accordingly, a sanitary system for retrieving barrier envelopes is required.

SUMMARY

It is an object of the present invention to provide a dispenser of barrier envelopes that reduces or minimizes the risk of spreading contaminants from a dental practitioner to his or her patients during the course of practicing dentistry. The purpose of the dispenser is to store a plurality of barrier envelopes within the body of the dispenser in order to protect the envelopes from coming into contact with contaminants such as bacteria, viruses and/or fungi that may be transmitted to the envelopes by the practitioner's hands, other contaminated objects nearby, and/or ambient air. The dispenser may be sterilized in order to maintain the envelopes in a sterile condition when the envelopes are initially loaded in the dispenser.

The dispenser includes a through opening for the purpose of providing access to the interior of its body such that a practitioner can retrieve the envelopes from the dispenser. The dispenser also includes a compressed spring in its interior for the purpose of pressing the envelopes against the opening in order to facilitate dispensal thereof.

Opposite ends of the spring are selectively connected to pusher plates that are configured to press the envelopes against the through opening. The pusher plates are also configured to be selectively coupled to one another with the spring being compressed in between the pusher plates in order to facilitate the process of loading the spring with the pushers inside of the dispenser.

The dispenser can be formed of two open-top box-like containers, or two halves, that are shaped and sized to be inserted inside of one another in order to create a protective enclosed space between them. The barrier envelopes are stored in the protective space.

The two halves can be slid against one another (e.g., toward one another) to form the protective enclosed spaced when the dispenser is in an unassembled state. The sliding motion can result in an interference fit between the two halves. The interference fit can be overcome by grasping the two halves by hand and pulling them away from one another by using a reasonable level of force to open the dispenser when needing to replenish the barrier envelopes.

BRIEF DESCRIPTION OF THE DRAWINGS

The above and other features of the present invention will become more apparent by describing in detail exemplary embodiments thereof in conjunction with the accompanying drawings, in which:

FIG. 1 is a perspective view illustrating an upper part of a barrier envelope dispenser according to an exemplary embodiment of the present invention;

FIG. 2 is an exploded perspective view illustrating the barrier envelope dispenser of FIG. 1;

FIG. 10 is a perspective view illustrating an upper part of a barrier envelope dispenser according to an exemplary embodiment of the present invention;

FIG. 11 is an exploded perspective view illustrating the barrier envelope dispenser of FIG. 10;

DETAILED DESCRIPTION OF THE EMBODIMENTS

Figure 3:
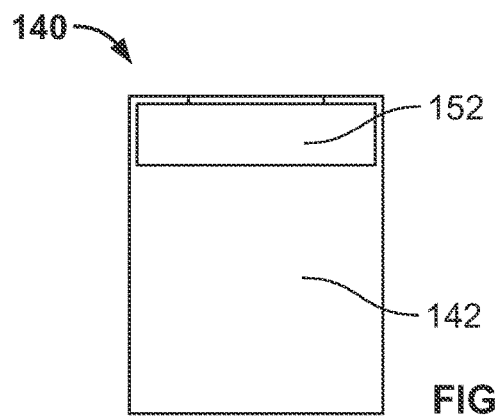
FIG. 3 is an elevational side view illustrating a first side of a casing component that forms a top part of the barrier envelope dispenser of FIG. 1.
Figure 4:
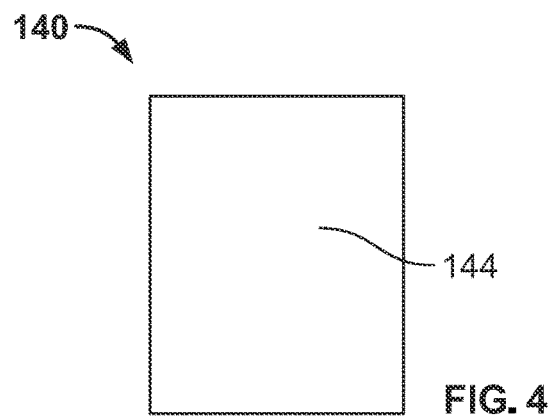
FIG. 4 is an elevational side view illustrating a second side of the casing component of FIG. 3, opposite to the side illustrated in FIG. 3.
Figure 5:
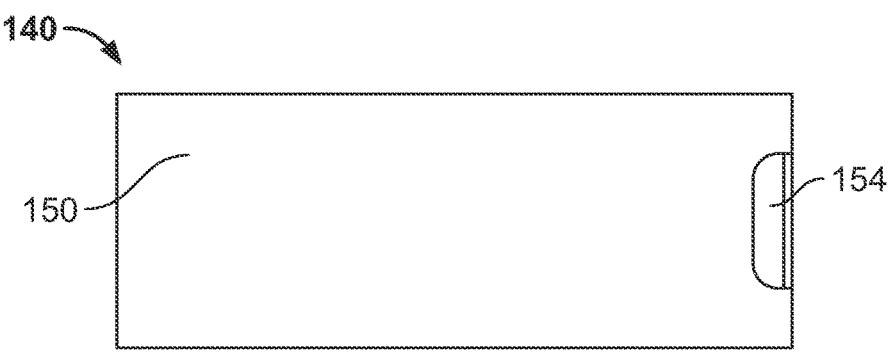
FIG. 5 is a top plan view illustrating a top side of the casing component of FIG. 3.
Figure 6:
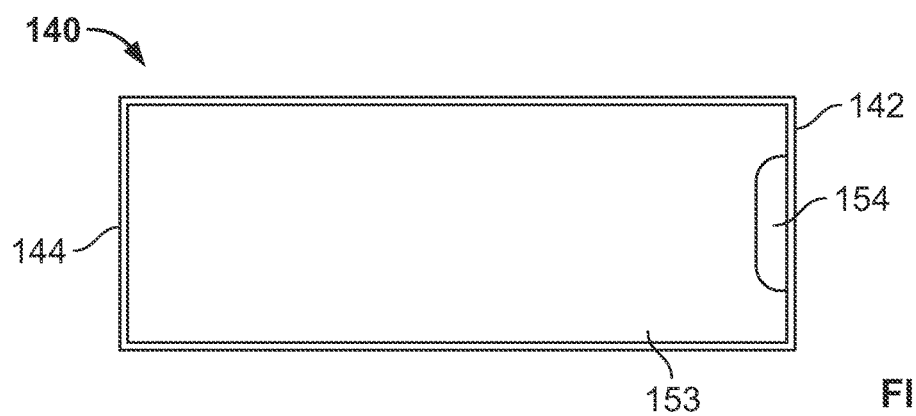
FIG. 6 is a bottom plan view illustrating an interior region of the casing component of FIG. 3.
Figure 7:
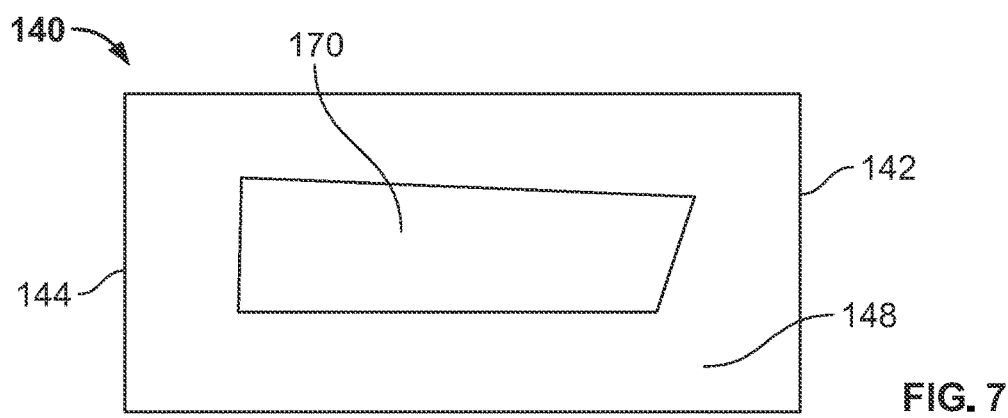
FIG. 7 is an elevational side view illustrating a third side of the cover of FIG. 3, extending between the first and second sides illustrated in FIGS. 3 and 4.

Exemplary embodiments of the present invention will be described more fully hereinafter with reference to the accompanying drawings. The present invention may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification. In addition, the dimensions illustrated in the drawings are non-limiting.

With reference to FIGS. 1-9, and more particularly to FIG. 2, a barrier envelope dispenser 100 of the present invention includes a first casing component 120, a second casing component 140, and an elastic member 160 disposed in an interior chamber of the barrier envelope dispenser 100.

Figure 9:
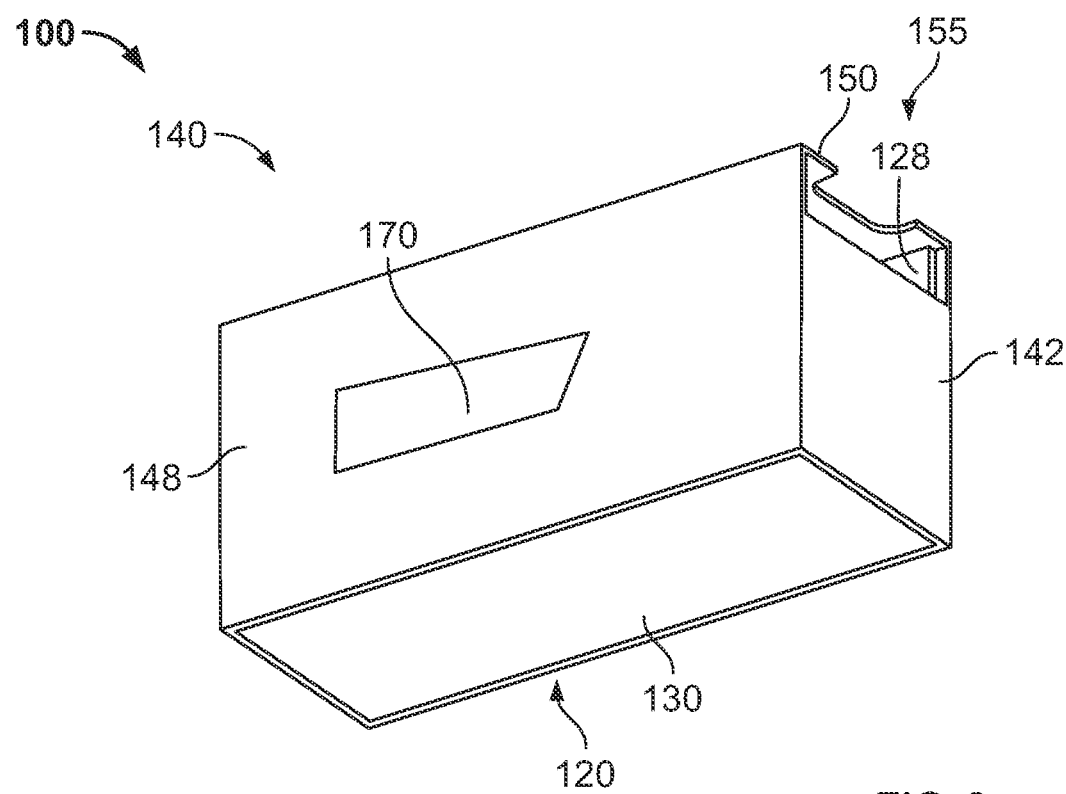
FIG. 9 is a perspective view illustrating a bottom part of the barrier envelope dispenser of FIG. 1.

The first casing component 120 and the second casing component 140, illustrated separately in FIG. 2, can be selectively coupled with one another in order to form the barrier envelope dispenser 100 as illustrated in FIGS. 1 and 9. When the first and second casing components 120 and 140 are selectively coupled to one another as illustrated in FIGS. 1 and 9, the resulting barrier envelope dispenser 100 may also be referred to as a casing. A plurality of barrier envelopes 180 may be disposed in the interior of the barrier envelope dispenser 100, as illustrated in FIGS. 1 and 2.

Referring to FIG. 1, the barrier envelope dispenser 100 includes a contiguous through opening 155 for dispensing the barrier envelopes 180. A user may retrieve the barrier envelopes 180, one-at-a-time or several-at-a-time, as needed, via the opening 155. As illustrated in FIG. 1, barrier envelope dispenser 100 encapsulates the barrier envelopes 180 all-around, thereby greatly reducing a contact area between a user's hands and the barrier envelopes 180. The opening 155, which is needed for providing access to the interior of the barrier envelope dispenser 100, exposes only a small surface area of a limited number of barrier envelopes 180. In more detail, as can be gleaned with reference to FIGS. 1-2, the opening 155 exposes only a narrow top surface of an upper portion 182 of a limited number of barrier envelopes 180, and exposes only a portion of a side surface of the upper portion 182 of a single barrier envelope 180 at a time.

A user would retrieve the barrier envelopes 180 from the dispenser 100 by manually contacting and pulling the envelopes 180 via the opening 155. In other words, a user would use his/her fingers to retrieve the envelopes 180 through the opening 155. Therefore, even when the user's hands are contaminated, the spreading of the contamination will be limited to the barrier envelope 180 being withdrawn because the user's fingers are not likely to come into contact with the envelopes 180 that are located behind the envelope 180 being retrieved, or, at most, have only a fleeting contact with the minute top surface of the upper portion 182 of a limited number of barrier envelopes 180 located behind the barrier envelope 180 being withdrawn.

This configuration greatly reduces the likelihood of spreading viruses, bacteria and/or fungi to a large number of envelopes 180 at once when retrieving one barrier envelope 180 from the dispenser 100. In contrast, if the barrier envelopes 180 were stored loosely in a large drawer, a user's hand(s) would likely contaminate a large number of envelopes 180 at once when accessing the drawer to retrieve one of the envelopes 180 (when the user's hands are contaminated).

The barrier envelope dispenser 100 of the present invention is intended to be utilized by a dentist. However, the barrier envelope dispenser 100 may also be utilized by other medical professionals who need to utilize sterile disposable barrier envelopes and would appreciate the benefit of eliminating or reducing the spread of contamination among the barrier envelopes 180 when making contact with a pool of loose barrier envelopes 180 for the purpose of retrieving a single envelope 180 from the pool.

The envelope dispenser 100 may be provided with a selective coupling mechanism for selectively attaching the dispenser 100 to or adjacent to, for example, a photostimulable phosphor (PSP) plate reader. A PSP plate would need to be protected by inserting the PSP plate inside of a barrier envelope 180 in a short period of time or immediately after the PSP plate is retrieved from a PSP plate reader (e.g., after being read and subsequently erased by the PSP reader). By selectively attaching the dispenser 100 to a PSP plate reader or adjacent/near the PSP plate reader, a dental professional can quickly and efficiently retrieve a barrier envelope 180 from the dispenser 100, retrieve a clean and/or erased PSP plate from the PSP reader, insert the PSP plate inside of the barrier envelope 180, and seal the barrier envelope 180.

The proximate vicinity between the PSP reader and the barrier envelope dispenser 100 would increase not only the working efficiency of a dental professional by reducing travel time between the location of the PSP reader and the location of barrier envelope 100, but would also reduce the likelihood of contaminating a PSP plate during travel (after being retrieved from the PSP reader and before being inserted in a barrier envelope 180) since the PSP plate would be exposed to the dental office environment only for a short period of time before being inserted in a barrier envelope 180.

FIGS. 1 and 2 illustrate a selective coupling mechanism 170 attached to a side of the barrier envelope dispenser 100. While it is exemplarily illustrated that the selective coupling mechanism 170 is attached to a side of the second casing component 140 (i.e., a third sidewall 148 of the second casing component 140), the present invention is not limited to this configuration. For example, the selective coupling mechanism 170 may be attached to other sides of the casing component 140. Alternatively, or in addition, the selective coupling mechanism 170 may be attached to any of the side surfaces (e.g., external side surfaces) of the first casing component 120. Further, more than one coupling mechanisms 170 may be attached to the exterior surfaces of any one of the first and/or second casing components 120 and 140 for the purpose of selectively attaching the barrier envelope dispenser 100 to a surface of a PSP reader or adjacent/near the PSP reader.

Referring to FIGS. 1, 2 and 9, the selective coupling mechanism 170 is a component of a hook and loop fastener. More specifically, the selective coupling mechanism 170 of FIGS. 1, 2 and 9 is exemplarily illustrated as being a strip of hooks which is configured to be selectively mated to a matching strip of loops (the matching strip of loops would be connected to a PSP reader or adjacent/near the PSP reader). This way, the dispenser 100 and the PSP reader can be selectively coupled to one another by mating the strip of hooks with the strip of loops.

It is understood that when using a hook and loop fastener, either a strip of hooks or a matching strip of loops may be selectively connected (e.g., adhered) to the barrier envelope dispenser 100, with the other strip being connected to/near the PSP reader.

While a hook and loop fastener is exemplarily described above, the selective coupling mechanism 170 may also be one selected from among a plurality of different types of selective fasteners, for example, a double-sided adhesive tape, adhesive (e.g., glue, whether permanent or washable), epoxy, a magnet (when both the barrier envelope dispenser 100 and a surface of the PSP reader or surface adjacent to or near the PSP reader are made of a ferromagnetic material), etc., or a combination thereof.

The first casing component 120 may be alternatively referred to as a bottom box. As illustrated in FIGS. 1-2, the first casing component 120 is configured to house the elastic member 160 and a plurality of barrier envelopes 180, disposed adjacent to the elastic member 160, in an interior area of the first casing component 120.

As can be gleaned with reference to FIGS. 1-2, the elastic member 160 is in a compressed state inside of the first casing component 120 in order to press the barrier envelopes 180 against a first sidewall 122 of the first casing component 120. Referring to FIGS. 1 and 2, the barrier envelopes 180 can be retrieved by hand via an opening 138 of the first casing component 120. As illustrated in FIGS. 1 and 2, the opening 138 of the first casing component 120 and openings 152 and 154 of the second casing component 140 together form the opening 155 of the envelope dispenser 100.

Figure 8:
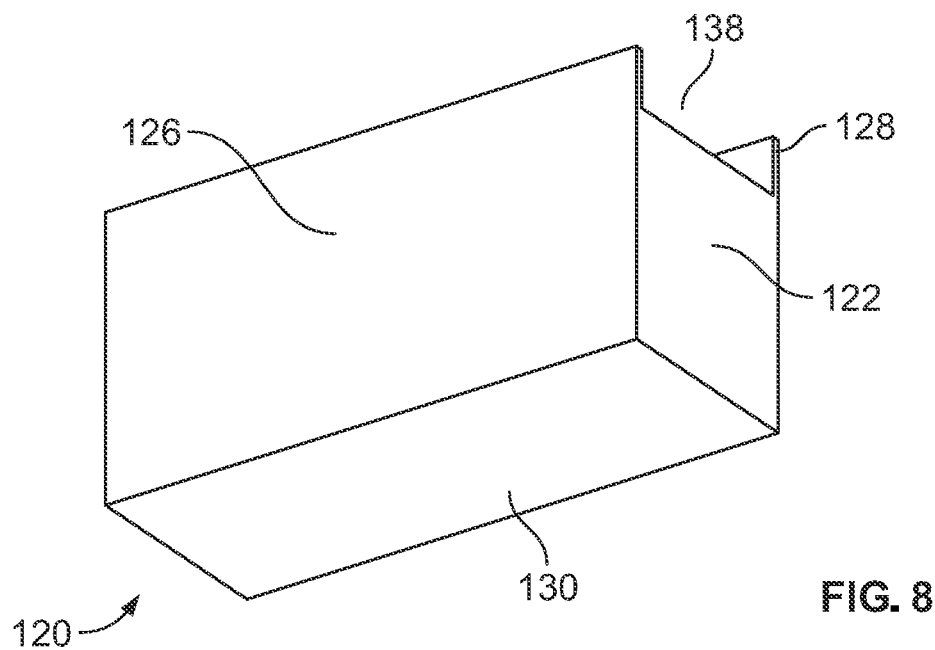
FIG. 8 is a perspective view illustrating an underside of a casing component that forms a bottom part of the barrier envelope dispenser of FIG. 1.

Referring to FIGS. 1 and 8, the first casing component 120 includes a first sidewall 122, a second sidewall 124, a third sidewall 126, a fourth sidewall 128, a fifth sidewall 130, and an open top 132. The elastic member 160 extends between the first and second sidewalls 122 and 124 in the interior of the first casing component 120. The barrier envelopes 180 are disposed between the elastic member 160 and the first sidewall 122 in the interior of the first casing component 120.

The open top 132 (see FIG. 2) provides access to the interior of the first casing component 120 such that the elastic member 160 and the barrier envelopes 162 can be inserted/loaded inside of the first casing component 120.

As illustrated in FIG. 1, the first sidewall 122 is shorter than the second sidewall 124 in order to form the opening 138. In addition, with reference to FIG. 1-2, the first casing component 120 includes a spacer insert 136 protruding from the first sidewall 122 in a direction toward the second sidewall 124. The spacer insert 136 serves to reduce the contact surface area between the envelope 180 that is exposed by the opening 155 and the first sidewall 122 in order to facilitate the process of dispensing (e.g., sliding) the exposed envelope 180 from the interior of the barrier envelope dispenser 100. In an embodiment, the spacer insert 136 may extend (or protrude) by ⅛ of an inch toward the second sidewall 124.

As illustrated in FIG. 8, the fifth sidewall 130 covers (e.g., closes) the bottom side of the first casing component 120 in order to prevent exposure of the envelopes 180 from the underside of the first casing component 120.

The first to fourth sidewalls 122-128 of the of the first casing component 120 may also be described as forming a hollow body of the first casing component 120, with the fifth sidewall 130 forming a closed of the hollow body and the open top 132 forming an open end of the hollow body.

Referring to FIG. 1, the elastic member 160 includes a first pusher 162 with keying ribs, a second pusher 164 with keying ribs, and a spring 166 extending between the first and second pushers 162 and 164. The first pusher 162 is configured to press against the second sidewall 124, and the second pusher 164 is configured to press the barrier envelopes 180 against the first sidewall 122.

The keying ribs of the first and second first pushers 162 and 164 aid in aligning and holding (e.g., attaching) the first and second first pushers 162 and 164 at the ends of the spring 166. This, in turn, facilitates a process of inserting the entire elastic member 160 into the interior chamber of the barrier envelope dispenser 100. The first and second first pushers 162 and 164 may be formed of a metal, wood, an elastomer, or a combination thereof. The metal can be, for example, stainless steel, titanium, aluminum, etc. The elastomer can be, for example, polycarbonate, polyvinyl chloride, and/or other suitable hard plastics.

The second casing component 140 may be referred to as a top box. Referring to FIGS. 2 and 3-7, the second casing component 140 includes a first sidewall 142, a second sidewall 144, a third sidewall 146, a fourth sidewall 148, a fifth sidewall 150 and an open bottom 153.

The first to fourth sidewalls 142-148 of the of the second casing component 140 may also be described as forming a hollow body of the second casing component 140, with the fifth sidewall 150 forming a closed of the hollow body and the open bottom 153 forming an open end of the hollow body.

The open bottom 153 enables the second casing component 140 to be selectively coupled to the first casing component 120. The coupling process may include, for example, aligning the first and second casing components 120 and 140 such that the open top 132 of the first casing component 120 faces the open bottom 153 of the second casing component 140, and inserting the first to fourth sidewalls 122-128 of the first casing component 120 in an interior of the second casing component 140 (i.e., in an interior space formed between the first to fourth sidewalls 142-148 of the second casing component 140).

The insertion process may include sliding the first to fourth sidewalls 122-128 of the first casing component 120 in the interior of the second casing component 140. After insertion, as can be gleaned by referring to FIGS. 1-2, the first to fourth sidewalls 122-128 of the first casing component 120 would overlap the first to fourth sidewalls 142-148 of the second casing component 140. In this configuration, the fifth sidewall 130 of the first casing component 120 and the fifth sidewall 150 of the second casing component 140 would be spaced apart from one another by the overlap between the first to fourth sidewalls 122-128 and first to fourth sidewalls 142-148, and together define opposite sides (or ends) of the barrier envelope dispenser 100. The interior surfaces of the first to fourth sidewalls 122-128 of the first casing component 120 would define four other sides (or ends) of the envelope dispenser 100 between the fifth sidewall 130 of the first casing component 120 and the fifth sidewall 150 of the second casing component 140.

Therefore, as can be gleaned by referring to FIGS. 1, 2 and 9, in an assembled state, the first to fifth sidewalls 122-130 of the first casing component 120 and the first to fifth sidewalls 142-150 of the second casing component 140 form an interior chamber of the barrier envelope dispenser 100.

The first and second casing components 120 and 140 can be sized and shaped such that the process of sliding the first to fourth sidewalls 122-128 of the first casing component 120 into the interior of the second casing component 140 requires a reasonable level of force to execute by hand. This force would be needed to overcome frictional forces generated by the first to fourth sidewalls 122-128 of the first casing component 120 pressing outwardly against the first to fourth sidewalls 142-148 of the second casing component 140 at the overlap therebetween.

Stated otherwise, the first and second casing components 120 and 140 can be sized and shaped to create an interference fit with one another. The interference fit can be sufficiently strong to prevent the first casing component 120 from sliding downwardly due to its own weight (e.g., by virtue of gravity) when the dispenser 100 is lifted upwardly or otherwise held in a manner which results in the first casing component 120 not being supported from underneath, but weak enough to allow a user to separate the first and second casing components 120 and 140 away from one another by using only a reasonable level of force.

As illustrated in FIGS. 1-4, 6 and 7, the first sidewall 142 of the second casing component 140 is shorter than the second sidewall 144 in order to form the opening 152 in the second casing component 140. In addition, the fifth sidewall 150 includes a notch forming the opening 154 adjacent to the first sidewall 142, as illustrated in FIG. 1-2. With reference to FIGS. 1-3, the openings 152 and 154 of the second casing component 140 form a contiguous open space.

The dispenser 100 and the envelopes 180 may be sterile. In one approach, the dispenser 100 can be regarded as a single use product that could be discarded and replaced by a new (and sterile) dispenser of barrier envelopes in order for the dispenser to be in a sterile condition or virtually in a sterile condition during use, (e.g., during the length of time that the envelopes 180 therein are being dispensed). Alternatively, the dispenser 100 may be manufactured by using materials that allow for subsequent sterilization in a dental office. In this case, the same dispenser 100 may be used repeatedly, subject to undergoing a sterilization process prior to being re-loaded with envelopes 180.

Each of the first casing component 120 and the second casing component 140 may be formed of a metal, an elastomeric material (e.g., plastic), wood, or a combination thereof. The metal may be, for example, aluminum, stainless steel, titanium, etc., or a combination thereof. The metal may be provided in sheet form.

In an embodiment, the first casing component 120 and the second casing component 140 are formed of sheet metal having a thickness of 0.06 inch. All of the edges of the first casing component 120 and the second casing component 140 may by manufactured to be dull, or not sharp. This would prevent the user's gloves and/or hands from being inadvertently cut when utilizing the dispenser 100. During the manufacturing process, for example, any burrs formed at the edges of the first and second casing components 120 and 140 would be removed, and/or sharp edges resulting from a shearing/cutting process of the sheet metal when forming the first and/or second casing components 120 and 140 would be rounded/dulled.

In an embodiment, the second casing component 140, which covers the first casing component 120, is 5.3 inches long, 1.99 inches wide, and 2.49 inches high. In this embodiment, the opening 152 is 1.87 inches long and 0.49 inches wide. The opening 154 is 1.06 inches long and 0.3 inches wide.

Figure 12:
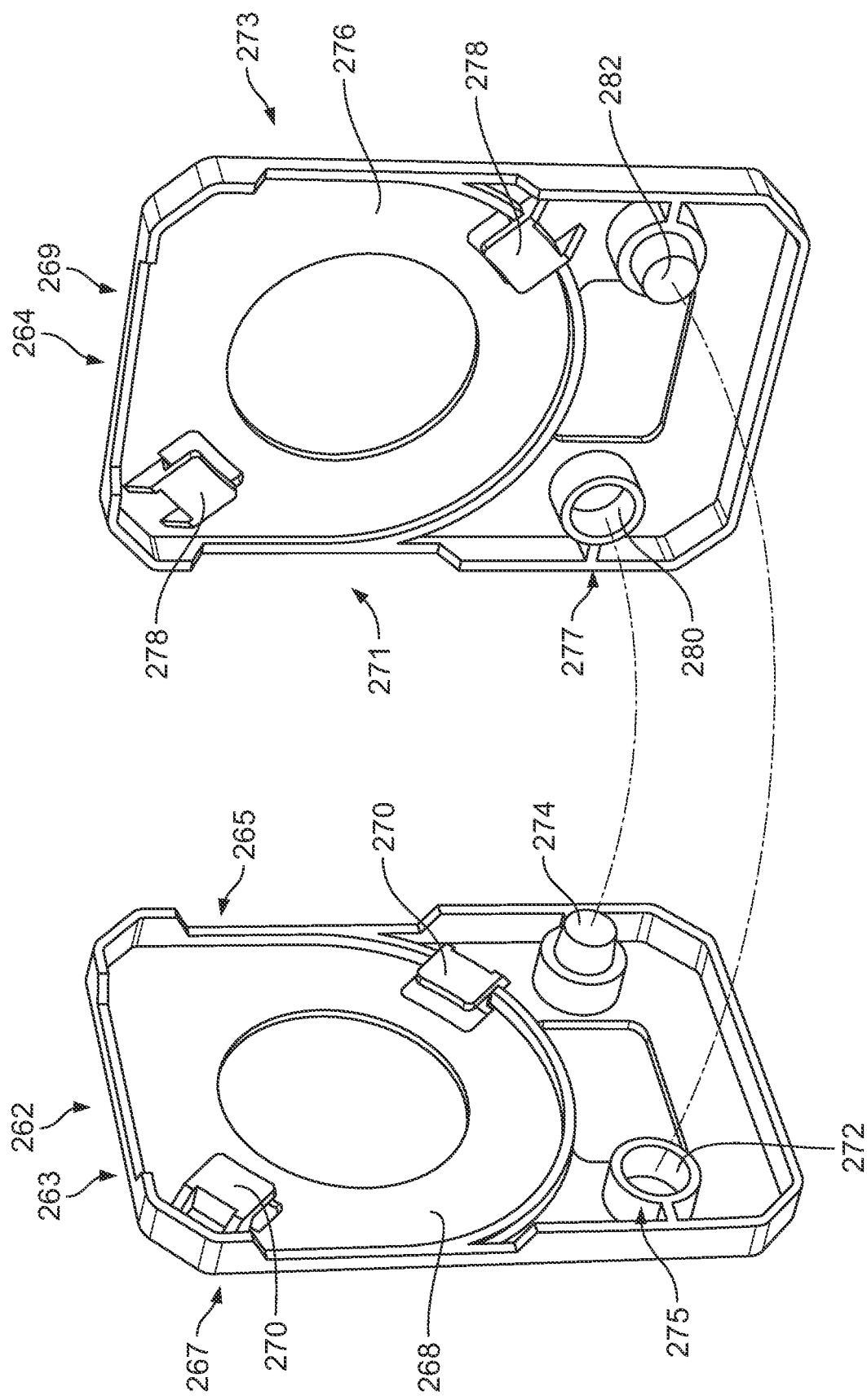
FIG. 12 is a magnified view illustrating pusher plates of an elastic member included in the barrier envelope dispenser of FIG. 10.

FIGS. 10-12 illustrate a barrier envelope dispenser 200 according to an exemplary embodiment. Aspects/components/parts of the barrier envelope dispenser 200 that are not described in detail below may be assumed to be similar to or the same as corresponding aspects/components/parts described elsewhere in this specification.

Referring to FIGS. 10 and 11, the barrier envelope dispenser 200 includes a first casing component 220, a second casing component 240, and an elastic member 260 disposed in an interior chamber of the barrier envelope dispenser 200 and configured to guide a plurality of barrier envelopes 280 toward a through opening 255 of the dispenser 200.

Referring to FIG. 11, the elastic member 260 includes a first pusher 262, a second pusher 264, and a spring 266 extending between and selectively connected to the first and second pushers 262 and 264.

The first and second pushers 262 and 264 are selectively connectable to one another, for example, by forming an interference fit with one another, while maintaining the spring 266 in a compressed state between the first and second pushers 262 and 264.

When the first and second pushers 262 and 263 are selectively connected to one another, the elastic member 260 can be inserted into an interior chamber of the dispenser 200 with ease since it is being inserted as one solid piece that is also relatively small in size. After the one-piece structure is inserted in the interior chamber, the first and second pushers 262 and 264 may then be separated from one another by pulling them apart from one another by hand. The first and second pushers 262 and 264 are configured such that only a reasonable amount of force is needed to separate them from one another.

The spring 266 has been omitted from FIG. 12 for clarity purposes, but it is understood that the spring 266 is selectively connected to the first and second pushers 262 and 264 of FIG. 12, as illustrated in FIG. 11. In other words, one end of the spring 266 is connected to the first pusher 262 and the other end of the spring 266 is connected to the second pusher 264.

Referring to FIGS. 11 and 12, and more particularly to FIG. 12, the first pusher 262 has a body 263 having a first side 265 facing the spring 266 and selectively connected to the spring 266, and a second side 267 opposite to the first side 265. As illustrated in FIG. 12, the first side 265 of the body 263 includes a flat surface 268 having a round perimeter, and a pair of connecting members 270 disposed at diametrically opposite ends of the perimeter of the flat surface 268.

Referring to FIG. 12, each connecting member 270 includes a portion that is raised over and covers a portion of the flat surface 268 for the purpose of maintaining the spring 266 selectively connected to the first pusher 262, as illustrated in FIG. 11. The connecting members 270 may also be referred to as hooks (or can otherwise be hook-like structures). Referring to FIG. 11, each end of the spring 266 may be flat (e.g., each end features a loop that stays flat during use), and one of the two flat ends of the spring 266 (e.g., a first end of the spring 266) may be inserted in the space between the flat surface 268 and the pair of connecting members 270 of the first pusher 262 in order to selectively connect the first end of the spring 266 to the first pusher 262.

Referring to FIGS. 11 and 12, and more particularly to FIG. 12, the second pusher 264 has a body 269 having a first side 271 facing the spring 266 and selectively connected to the spring 266, and a second side 273 opposite to the first side 271. As illustrated in FIG. 12, the first side 271 of the body 269 includes a flat surface 276 having a round perimeter, and a pair of connecting members 278 disposed at diametrically opposite ends of the perimeter of the flat surface 276.

Referring to FIG. 12, each connecting member 278 includes a portion that is raised over and covers a portion of the flat surface 276 for the purpose of maintaining the spring 266 selectively connected to the second pusher 264, as illustrated in FIG. 11. The connecting members 278 may also be referred to as hooks (or can otherwise be hook-like structures). Referring to FIG. 11, a second end of the spring 266—opposite to the first end of the spring 266 connected to the first pusher 262—may be inserted in the space between the flat surface 276 and the pair of connecting members 278 of the second pusher 264 in order to selectively connect the second end of the spring 266 to the second pusher 264.

Referring to FIG. 12, an annular member 274 protrudes away from the first side 265 of the first pusher 262. In addition, as illustrated in FIG. 12, a hollow annular member 275 protrudes away from the first side 265 of the first pusher 262, defining an interior cavity 272 in the annular member 275. The annular members 274 and 275 are spaced apart from one another.

Referring to FIG. 12, an annular member 282 protrudes away from the first side 271 of the second pusher 264. In addition, as illustrated in FIG. 12, a hollow annular member 277 protrudes away from the first side 271 of the second pusher 264, defining an interior cavity 280 in the annular member 277. The annular members 277 and 282 are spaced apart from one another.

As can be gleaned by referring to FIG. 12, the cavity 280 of the hollow member 277 of the second pusher 264 is configured to selectively receive the annular member 274 of the first pusher 262 therein. In addition, the cavity 272 of the hollow member 275 of the first pusher 262 is configured to selectively receive the annular member 282 therein. Therefore, the first and second pushers 262 and 264 can be selectively coupled to one another—with the spring 266 compressed therebetween—by forcing the first and second pushers 262 and 264 toward one another until the cavity 280 receives the annular member 274 therein and the cavity 272 receives the annular member 282 therein.

The annular members 274, 275, 277 and 282 can be shaped and sized in order to create an interference fit therebetween. The interference fit can be strong enough to resist the pushing force of the compressed spring 266 such that the first and second pushers 262 and 264 do not spring away from one another as soon as the user stops applying compressive force to the spring 266. Therefore, the entire elastic member 260 can be conveniently inserted in the interior chamber of the dispenser 200 in a small form factor by using only one hand, sparing the user from the dexterity that is otherwise required to compress the spring 266 while simultaneously maintaining the spring 266 straight (e.g., keeping the spring 266 from bending or buckling while being compressed) during the process of inserting the elastic member 260 in the interior chamber of the dispenser 260.

Alternatively, the interference fit between the annular members 274, 275, 277 and 282 can be somewhat weaker, which would require the user to apply some compressive force to the first and second pushers 262 and 264 to keep them from springing away from one another once selectively coupled to one another. However, even in this case the user can utilize only one hand to maintain the first and second pushers 262 and 264 compressed against one another while (e.g., with two fingers respectively pressing the first and second pushers 262 and 264 against one another) while simultaneously inserting the elastic member 260 inside of the interior chamber of the dispenser 200.

The annular members 274, 275, 277 and 282, when coupled to one another, prevent the first and second pushers 262 and 264 from rotating relative to one another, thereby sparing the user from having to utilize two hands to ensure that the first and second pushers 262 and 264 do not move relative to one another during the insertion process. This may also prevent or reduce the likelihood of the compressed spring 266 unexpectedly buckling (or shooting out from between the first and second pushers 262 and 264) during the insertion process.

While the members 274, 275, 277 and 282 are described as being annular, it is understood that members 274, 275, 277 and 282 may also have different shapes, for example, matching cuboid shapes, or other kinds of cross-sectional shapes along their respective lengths that permit the members 274, 275, 277 and 282 to be selectively coupleable with one another.

In addition, while the first and second pushers 262 and 264 are illustrated as having two coupling members each, the first and second pushers 262 and 264 can also have three or more coupling members each.

In FIGS. 11 and 12 it is illustrated that each one of the first and second pushers 262 and 264 includes a female coupling member and a male coupling member (e.g., the members 274 and 282 are male and the members 275 and 277 are female). However, the present invention is not limited to this configuration. For example, the first pusher 262 can be configured to have female couplers only or male couplers only, with the second pusher 264 being configured to have matching male couplers only or female couplers only, depending on the configuration of the first pusher 262.

Figure 13:
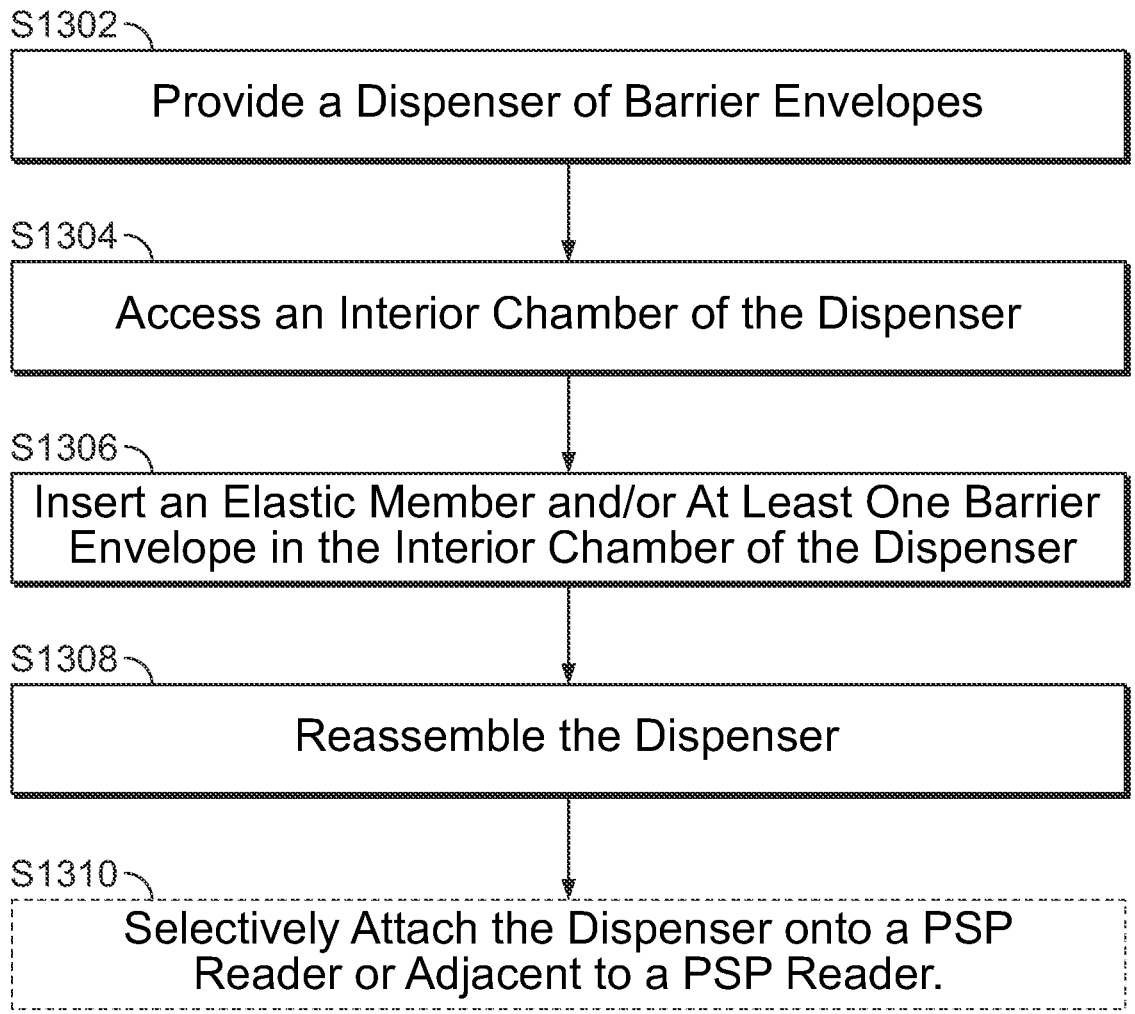
FIG. 13 is a diagram illustrating a method of utilizing a barrier envelope dispenser according to an exemplary embodiment of the present invention.

FIG. 13 illustrates method steps for utilizing a barrier envelope dispenser according to an exemplary embodiment of the present invention;

Referring to FIG. 13, operation S1302 includes providing a dispenser of barrier envelopes such as the dispenser 100 or 200 described above.

Operation S1304 includes accessing an interior chamber of the dispenser. This operation can be accomplished by grasping both the first and second casing components 120 and 140, or 220 and 240, as the case may be, and pulling the first and second casing components 120/220 and 140/240 away from one another in order to separate them from one another.

Operation S1306 may include inserting an elastic member 160 or 260 inside the interior chamber when the elastic member 160 or 260 is not present in the chamber, and may also include inserting at least one barrier envelope 180 or 280 within the interior chamber.

Operation S1306 may include applying force to the first and second pushers 262 and 264 to direct the first and second pushers 262 and 264 toward one another until the first and second pushers 262 and 264 become selectively coupled to one another with the spring 266 compressed therebetween, as described above.

Operation S1306 may also include uncoupling the first and second pushers 262 and 264 away from one another once that the elastic member 260 has been inserted into the interior chamber in order for the elastic member 260 to guide barrier envelopes toward the through opening of the dispenser.

When utilizing the elastic member 160, operation S1306 may include pressing the first and second pushers 162 and 164 toward one another while ensuring that the spring 166 does not buckle away from in between them, and inserting the elastic member 160 inside of the interior chamber.

Operation S1308 includes reassembling the dispenser 100 or 200 by selectively coupling the first and second casing components 120/220 and 140/240 to one another as described above.

Operation S1310 includes selectively attaching the dispenser 100 or 200 onto a PSP reader or adjacent to a PSP reader. Operation 1310 may include selectively attaching a coupling member to an external side of the dispenser 100/200, as described above, and then selectively attaching the dispenser 100/200 to a surface of a PSP reader or adjacent to the PSP reader. Operation S1310 may be optional.

While the present invention has been particularly shown and described with reference to exemplary embodiments thereof, it will be apparent to those of ordinary skill in the art that various changes in form and detail may be made therein without departing from the spirit and scope of the present invention.

What is claimed is:

1. A barrier envelope dispenser configured for use in dentistry, the barrier envelope dispenser comprising:
    a casing defining an exterior of the barrier envelope dispenser and an interior chamber in the barrier envelope dispenser, the casing including an opening therethrough which connects the interior chamber with the exterior of the barrier envelope dispenser; and
    an elastic member disposed in the interior chamber and configured to guide one or more barrier envelopes in the interior chamber toward the through opening such that the one or more barrier envelopes can be selectively retrieved from the interior chamber via the through opening,
    wherein the casing includes: a first casing component and a second casing component,
    wherein the first casing component has a hollow body with a first closed end and a second open end opposite to the first closed end,
    wherein the second casing component has a hollow body with a first closed end and a second open end opposite to the first closed end, and
    wherein, when the casing is in an assembled state, the hollow bodies of the first and second casing components overlap one another, and the first closed ends of the first and second casing components, respectively, are arranged at opposite sides of the casing with at least a portion of the overlap between the hollow bodies of the first and second casing components extending therebetween,
    wherein the hollow body of the second casing component includes a first side and a second side opposite to the first side, the first and second sides of the second casing component delimiting opposite ends of the interior chamber,
    wherein the elastic member includes:
    a first pusher;
    a second pusher; and
    a spring extending between the first and second pushers and between the first and second sides of the second casing component, the spring being configured to be in a compressed state such that the first pusher or the second pusher can direct the one or more barrier envelopes in the interior chamber toward the through opening such that the one or more barrier envelopes can be selectively retrieved from the interior chamber via the through opening.

2. The barrier envelope dispenser of claim 1, wherein the through opening extends through the hollow body of the first casing component and through the hollow body of the second casing component.

3. The barrier envelope dispenser of claim 2, wherein the through opening further extends through a portion of the first closed end of the first casing component.

4. The barrier envelope dispenser of claim 1, wherein the first and second casing components are slidably engaged with one another.

5. The barrier envelope dispenser of claim 1, wherein the first casing component and the second casing component form an interference fit therebetween at the overlap between the respective hollow bodies thereof.

6. The barrier envelope dispenser of claim 1, further comprising an elongated spacer protruding from the first side of the second casing component and extending into the interior chamber.

7. The barrier envelope dispenser of claim 6, wherein the elongated spacer is disposed adjacent to the through opening at the first side of the second casing component.

8. The barrier envelope dispenser of claim 1, wherein the first pusher includes a first coupling member and a second coupling member extending from a side of the first pusher that faces the spring, the second pusher includes a third coupling member and a fourth coupling member extending from a side of the second pusher that faces the spring, wherein the first coupling member is configured to be selectively coupleable with the third coupling member and the second coupling member is configured to be selectively coupleable with the fourth coupling member such that the first and second pushers can be selectively coupled to one another with the spring in a compressed state therebetween.

9. The barrier envelope dispenser of claim 1, further comprising a connecting member attached to the exterior of the casing,
    wherein the connecting member is configured to selectively connect the casing to a supporting surface.

10. A method for utilizing a dispenser of barrier envelopes in dentistry, the method comprising:
    providing a dispenser of barrier envelopes;
    accessing an interior chamber of the dispenser; and
    inserting at least one barrier envelope within the interior chamber,
    wherein the dispenser includes:
    a casing defining an exterior of the dispenser and the interior chamber in the dispenser, the casing including an opening therethrough which connects the interior chamber with the exterior of the dispenser; and
    an elastic member disposed in the interior chamber and configured to guide the at least one barrier envelope toward the through opening such that the at least one barrier envelope can be selectively retrieved from the interior chamber via the through opening.

11. The method of claim 10, wherein the casing includes:
    a first casing component having a hollow body with a first closed end and a second open end opposite to the first closed end, and
    a second casing component having a hollow body with a first closed end and a second open end opposite to the first closed end, wherein, when the casing is in an assembled state, the hollow body of the first casing component overlaps the hollow body of the second casing component, and the first closed ends of the first and second casing components, respectively, are arranged at opposite ends of the casing with at least a portion of the overlap between the hollow bodies of the first and second casing components extending therebetween.

12. The method of claim 11, further comprising the step of closing the interior chamber of the casing, said step comprising:
    arranging the second open end of the first casing component to face the second open end of the second casing component; and
    inserting the hollow body of the second casing component into the hollow body of the first casing component through the second open end of the first casing component such that the hollow bodies of the first and second casing components overlap one another.

13. The method of claim 12, further comprising the step of retrieving the at least one barrier envelope from the interior chamber of the dispenser via the opening which connects the interior chamber with the exterior of the dispenser.

14. The method of claim 11, wherein, when the dispenser is in an assembled state, the step of accessing the interior chamber of the casing includes separating the first and second casing components away from one another until the bodies of the first and second casing components no longer overlap one another.

15. The method of claim 14, wherein the separation process includes sliding the first and second casing components away from one another.

16. The method of claim 10, further comprising the step of attaching a connecting member to the exterior of the dispenser, the connecting member being configured to selectively connect the dispenser to a supporting surface.

17. The method of claim 16, further comprising the step of selectively connecting the dispenser to the supporting surface.

18. The method of claim 16, wherein the connecting member is selected from the group consisting of a hook and loop fastener, a double-sided adhesive tape, adhesive, epoxy, and a magnet.

19. A barrier envelope dispenser configured for use in dentistry, the barrier envelope dispenser comprising:
    a casing defining an exterior of the barrier envelope dispenser and an interior chamber in the barrier envelope dispenser, the casing including an opening therethrough which connects the interior chamber with the exterior of the barrier envelope dispenser; and
    an elastic member disposed in the interior chamber and configured to guide one or more barrier envelopes in the interior chamber toward the through opening such that the one or more barrier envelopes can be selectively retrieved from the interior chamber via the through opening,
    wherein the casing includes: a first casing component and a second casing component,
    wherein the first casing component has a hollow body with a first closed end and a second open end opposite to the first closed end,
    wherein the second casing component has a hollow body with a first closed end and a second open end opposite to the first closed end, and
    wherein, when the casing is in an assembled state, the hollow bodies of the first and second casing components overlap one another, and the first closed ends of the first and second casing components, respectively, are arranged at opposite sides of the casing with at least a portion of the overlap between the hollow bodies of the first and second casing components extending therebetween,
    wherein the hollow body of the second casing component includes a first side and a second side opposite to the first side, the first and second sides of the second casing component delimiting opposite ends of the interior chamber, and
    wherein the second casing component includes an elongated spacer protruding from the first side of the second casing component and extending into the interior chamber.

20. The barrier envelope dispenser of claim 19, wherein the elongated spacer is disposed adjacent to the through opening at the first side of the second casing component.

* * * * *